United States Patent

Cantatore

[11] 4,442,250
[45] Apr. 10, 1984

[54] PIPERIDYL DERIVATIVES OF MACROCYCLIC TRIAZINE COMPOUNDS, POSSESSING A STABILIZING ACTIVITY FOR POLYMERS, AND PROCESSES FOR THEIR PREPARATION

[75] Inventor: Giuseppe Cantatore, Casalecchio di Reno, Italy

[73] Assignee: Chimosa Chimica Organica S.p.A., Pontecchio Marconi, Italy

[21] Appl. No.: 426,153

[22] Filed: Sep. 28, 1982

[30] Foreign Application Priority Data

Oct. 2, 1981 [IT] Italy ............... 24296 A/81

[51] Int. Cl.³ .................. C07D 401/14; C08K 5/34
[52] U.S. Cl. .................. 524/98; 524/100; 544/198; 544/209
[58] Field of Search ............... 524/98, 100; 544/198, 544/209

[56] References Cited

U.S. PATENT DOCUMENTS

| | | | |
|---|---|---|---|
| 4,086,204 | 4/1978 | Cassandrini et al. | 524/100 |
| 4,238,388 | 12/1980 | Cantatore et al. | 524/98 |
| 4,251,435 | 2/1981 | Son et al. | 524/102 |
| 4,279,804 | 7/1981 | Cantatore et al. | 524/102 |
| 4,288,593 | 9/1981 | Rody | 524/100 |
| 4,316,025 | 2/1982 | Cantatore et al. | 524/98 |
| 4,366,277 | 12/1982 | Molt | 524/102 |
| 4,376,836 | 3/1983 | Wiezer et al. | 524/100 |

Primary Examiner—John Kight, III
Assistant Examiner—R. A. White
Attorney, Agent, or Firm—Wenderoth, Lind & Ponack

[57] ABSTRACT

Novel piperidine derivatives of macrocyclic triazine compounds of the formula

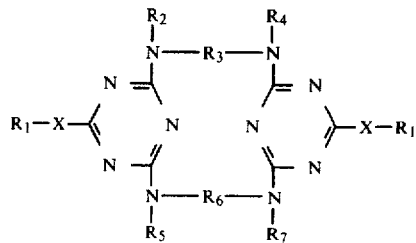

in which $R_1$, $R_2$, $R_3$, $R_4$, $R_5$, $R_6$, $R_7$ and X are as defined in the description, have been prepared. These compounds possess a light-stabilizing, heat-stabilizing and oxidation-stabilizing activity for synthetic polymers, in particular for hydrocarbon polymers.

18 Claims, No Drawings

PIPERIDYL DERIVATIVES OF MACROCYCLIC TRIAZINE COMPOUNDS, POSSESSING A STABILIZING ACTIVITY FOR POLYMERS, AND PROCESSES FOR THEIR PREPARATION

The present invention relates to novel piperidine derivatives of macrocyclic triazine compounds, which derivatives are useful as light stabilisers, heat stabilisers and oxidation stabilisers for synthetic polymers, and to processes for their preparation.

More precisely, the present invention relates to compounds of the general formula (I):

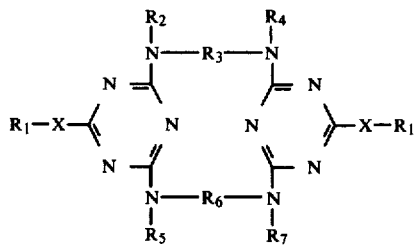

in which $R_1$ is hydrogen, $C_1$–$C_{18}$-alkyl, $C_3$–$C_{18}$-alkenyl, $C_5$–$C_{18}$-cycloalkyl, substituted or unsubstituted $C_6$–$C_{18}$-aryl, substituted or unsubstituted $C_7$–$C_{18}$-aralkyl, an —$R_8$—Y radical, in which $R_8$ is $C_2$–$C_6$-alkylene and Y is —O—$R_9$ or

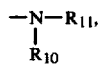

$R_9$ being hydrogen or $C_1$–$C_{18}$-alkyl and $R_{10}$ and $R_{11}$, which may be identical or different, being $C_1$–$C_6$-alkyl, 2,2,6,6-tetramethyl-piperid-4-yl or 1,2,2,6,6-pentamethylpiperid-4-yl, or $R_1$ is a radical of the formula (II)

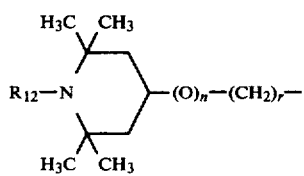

in which n is zero or 1, r is zero, 1, 2 or 3, $R_{12}$ is hydrogen, $C_1$–$C_{12}$-alkyl, $C_3$–$C_{12}$-alkenyl or -alkynyl, substituted or unsubstituted $C_7$–$C_{12}$-aralkyl, $C_1$–$C_{12}$-acyl, 2,3-epoxypropyl or

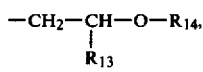

in which $R_{13}$ is hydrogen, methyl, ethyl or phenyl and $R_{14}$ is hydrogen, $C_1$–$C_{12}$-alkyl, $C_3$–$C_{12}$-alkenyl, $C_7$–$C_{12}$-aralkyl or $C_1$–$C_{12}$-acyl, or $R_1$ is a radical of the formula (III)

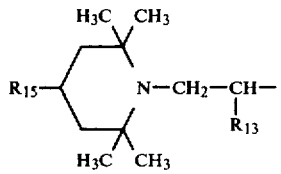

in which $R_{15}$ is hydrogen, $C_1$–$C_8$-alkoxy, $C_3$–$C_8$-alkenyloxy or benzyloxy and $R_{13}$ is as defined above, and X is >O, >S or >N—$R_{16}$, in which $R_{16}$ has the meaning as $R_1$, and the radical $R_1$—X—, considered as a whole, can also be chlorine or pyrrolidin-1-yl, piperidin-1-yl or hexahydroazepin-1-yl, $R_2$, $R_4$, $R_5$ and $R_7$, which may be identical or different, are hydrogen, $C_1$–$C_{12}$-alkyl, $C_2$–$C_6$-hydroxyalkyl, $C_3$–$C_{12}$-alkenyl, $C_5$–$C_{12}$-cycloalkyl, substituted or unsubstituted $C_6$–$C_{12}$-aryl, substituted or unsubstituted $C_7$–$C_{12}$-aralkyl or a radical of the formula (II), and $R_3$ and $R_6$, which may be identical or different, are $C_2$–$C_{12}$-alkylene, $C_4$–$C_{12}$-iminodialkylene or -oxadialkylene, $C_5$–$C_{12}$-cycloalkylene, $C_6$–$C_{12}$-arylene or $C_7$–$C_{12}$-aralkylene, and at least one of the radicals $R_1$, $R_2$, $R_4$, $R_5$ and $R_7$ in formula (I) is a radical of the formula (II).

Illustrative examples of the meanings of the various radicals shown in formulae (I), (II) and (III) are as follows:

$R_1$ and $R_{16}$: hydrogen, methyl, ethyl, propyl, isopropyl, butyl, but-2-yl, isobutyl, hexyl, octyl, decyl, dodecyl, hexadecyl, octadecyl, allyl, methallyl, but-2-enyl, undec-10-enyl, oleyl, cyclohexyl, 2- or 4-methylcyclohexyl, 3,3,5-trimethylcyclohexyl, cyclooctyl, cyclododecyl, phenyl, o-, m- and p-methylphenyl, 2,6-dimethylphenyl, 2,4,6-trimethylphenyl, 4-t-butylphenyl, 4-t-octylphenyl, 4-methoxyphenyl, 4-ethoxyphenyl, 3,5-di-t-butyl-4-hydroxyphenyl, benzyl, 4-methylbenzyl, 4-t-butylbenzyl, 4-hydroxybenzyl, 3,5-di-t-butyl-4-hydroxybenzyl, 2,2,6,6-tetramethyl-piperid-4-yl, 1,2,2,6,6-pentamethyl-piperid-4-yl, 1-allyl-2,2,6,6-tetramethyl-piperid-4-yl, 1-benzyl-2,2,6,6-tetramethyl-piperid-4-yl, 1-acetyl-2,2,6,6-tetramethyl-piperid-4-yl, 2-(2,2,6,6-tetramethyl-piperid-4-yl)-ethyl, (2,2,6,6-tetramethyl-piperid-1-yl)-ethyl and 3-(2,2,6,6-tetramethyl-piperid-4-yloxy)-propyl.

$R_2$, $R_4$, $R_5$ and $R_7$: hydrogen, methyl, ethyl, propyl, isopropyl, butyl, but-2-yl, isobutyl, hexyl, octyl, decyl, dodecyl, 2-hydroxyethyl, 2-hydroxypropyl, 2-hydroxybutyl, allyl, methallyl, but-2-enyl, hex-2-enyl, undec-10-enyl, cyclohexyl, 2- or 4-methylcyclohexyl, 3,3,5-trimethylcyclohexyl, cyclooctyl, cyclododecyl, phenyl, o-, m- and p-methylphenyl, p-methoxyphenyl, p-ethoxyphenyl, benzyl, 4-methylbenzyl, 4-t-butylphenyl, 2,2,6,6-tetramethyl-piperid-4-yl, 1,2,2,6,6-pentamethyl-piperid-4-yl, 1-allyl-2,2,6,6-tetramethyl-piperid-4-yl, 1-benzyl-2,2,6,6-tetramethyl-piperid-4-yl and 1-acetyl-2,2,6,6-tetramethyl-piperid-4-yl.

$R_3$ and $R_6$: ethylene, 1,2- or 1,3-propylene, 2-hydroxy-1,3-propylene, tetramethylene, pentamethylene, 2,2-dimethyl-1,3-propylene, hexamethylene, octamethylene, decamethylene, dodecamethylene, 2,2,4- and 2,4,4-trimethylhexamethylene, 3-oxa-1,5-pentylene, 4-oxa-1,7-heptylene, iminodiethylene, iminodipropylene, 1,2-, 1,3- and 1,4-cyclohexylene, 1,3- and 1,4-cyclohexylenedimethylene, o-, m- and p-phenylene and o-, m- and p-xylylene.

$R_8$: ethylene, 1,2- and 1,3-propylene, tetramethylene and hexamethylene.

R₉: hydrogen, methyl, ethyl, propyl, butyl, hexyl, heptyl, octyl, 2-ethylhexyl, decyl, dodecyl, hexadecyl and octadecyl.

R₁₀ and R₁₁: methyl, ethyl, propyl, butyl, hexyl, 2,2,6,6-tetramethyl-piperid-4-yl and 1,2,2,6,6-pentamethylpiperid-4-yl.

R₁₂: hydrogen, methyl, ethyl, propyl, butyl, hexyl, octyl, decyl, dodecyl, allyl, methallyl, but-2-enyl, hex-2-enyl, propargyl, benzyl, 4-methylbenzyl, 4-t-butylbenzyl, 4-hydroxybenzyl, acetyl, propionyl, butyryl, caproyl and benzoyl.

R₁₃: hydrogen, methyl, ethyl and phenyl.

R₁₄: hydrogen, methyl, ethyl, propyl, butyl, hexyl, heptyl, octyl, 2-ethylhexyl, decyl, dodecyl, allyl, methallyl, but-2-enyl, hex-2-enyl, undec-10-enyl, benzyl, 4-methylbenzyl, 4-t-butylbenzyl, acetyl, propionyl, butyryl, caproyl and benzoyl.

R₁₅: hydrogen, methoxy, ethoxy, propoxy, butoxy, hexyloxy, octyloxy, allyloxy, methallyloxy and benzyloxy.

Preferred compounds of the formula (I) are those in which R₁ and R₁₆, which may be identical or different, are C₁-C₁₂-alkyl, C₃-C₁₂-alkenyl, C₅-C₁₂-cycloalkyl, C₆-C₁₂-aryl, C₇-C₁₂-aralkyl, 2,2,6,6-tetramethyl-piperid-4-yl or 1,2,2,6,6-pentamethyl-piperid-4-yl, R₂, R₄, R₅ and R₇, which may be identical or different, are C₁-C₄-alkyl, C₂-C₃-hydroxyalkyl, C₃-C₆-alkenyl, C₅-C₈-cycloalkyl, C₆-C₈-aryl, C₇-C₁₂-aralkyl, 2,2,6,6-tetramethyl-piperid-4-yl or 1,2,2,6,6-pentamethyl-piperid-4-yl, R₃ and R₆, which may be identical or different, are C₂-C₆-alkylene, C₄-C₆-iminodialkylene or C₄-C₆-oxadialkylene, R₈ is C₂-C₄-alkylene, R₉ is hydrogen or C₁-C₁₂-alkyl, R₁₀ and R₁₁, which may be identical or different, are C₁-C₄-alkyl, 2,2,6,6-tetramethyl-piperid-4-yl or 1,2,2,6,6-pentamethyl-piperid-4-yl, R₁₂ is hydrogen, C₁-C₆-alkyl, C₃-C₆-alkenyl or -alkynyl, benzyl, C₁-C₆-acyl, 2,3-epoxypropyl or 2-hydroxyethyl, R₁₃ is hydrogen or methyl, R₁₄ is hydrogen, C₁-C₆-alkyl, C₃-C₆-alkenyl, benzyl or C₁-C₆-acyl, and R₁₅ is hydrogen, C₁-C₆-alkoxy, allyloxy or benzyloxy.

R₁—X—, considered as a whole, is preferably chlorine, piperid-1-yl or hexahydroazepin-1-yl.

Particularly preferred compounds of the formula (I) are those in which X is >O or >N—R₁₆, R₁ and R₁₆, which may be identical or different, are hydrogen, C₂-C₁₂-alkyl, cyclohexyl, 2,2,6,6-tetramethyl-piperid-4-yl or 1,2,2,6,6-pentamethyl-piperid-4-yl, R₂, R₄, R₅ and R₇, which may be identical or different, are hydrogen, 2,2,6,6-tetramethyl-piperid-4-yl or 1,2,2,6,6-pentamethyl-piperid-4-yl, R₃ and R₆ are C₂-C₆-alkylene, R₈ is C₂-C₃-alkylene, R₁₀ and R₁₁, which may be identical or different, are C₁-C₄-alkyl, 2,2,6,6-tetramethyl-piperid-4-yl or 1,2,2,6,6-pentamethyl-piperid-4-yl, R₁₂ is hydrogen or methyl and R₁—X—, considered as a whole, is chlorine, piperid-1-yl or hexahydroazepin-1-yl.

The Applicant has already described, in U.S. Pat. No. 4,086,024, the preparation, and use as stabilisers, of piperidyl-triazine polymers, for example those of the formula:

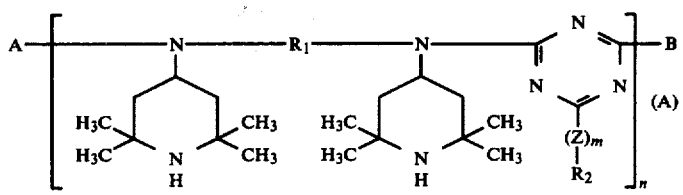

These polymers consist of mixtures of oligomers of various molecular weights; however, their composition is complex and not precisely reproducible.

The polymers of U.S. Pat. No. 4,086,204 were prepared from cyanuric chloride, a diamine of the formula HX—R₁—YH and a compound of the formula R₂—ZH, in accordance with two alternative methods, which respectively provide first reacting cyanuric chloride with the compound HX—R₁—YH or with the compound R₂—ZH and then reacting the intermediate, thus formed, with the other reagent. In each case, the process was carried out in two stages and, in the case where the first stage provides the reaction between cyanuric chloride and the diamine, the intermediate is also a mixture of polymeric products.

The Applicant has now found—and this is a further subject of the present invention—that if cyanuric chloride is reacted with a diamine of the formula

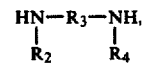

with a diamine of the formula

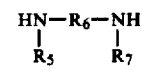

and with a compound of the formula R₁—XH, in which R₁, R₂, R₃, R₄, R₅, R₆, R₇ and X are as defined above, in a three-stage process, under critical and well-defined reaction conditions, well-defined intermediates are formed, and the compounds of the formula (I) are obtained as the final product.

The novel process which forms a subject of the present invention can be carried out in accordance with two alternatives. In the first alternative, the process is carried out as follows:

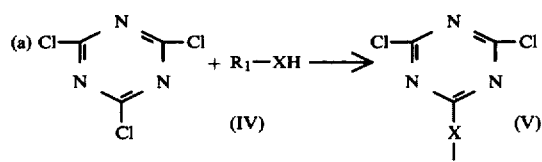

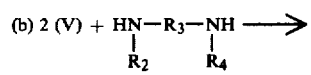

(VI)

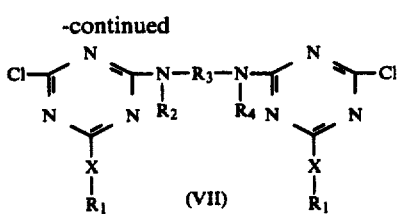

(c) (VII) + HN—R₆—NH  ⟶ compounds of the formula (I).
      |      |
      R₅    R₇
      (VIII)

This thus provides the preparation, from cyanuric chloride and reagent (IV), of a dichlorotriazine (V), which is then condensed with a diamine (VI) to give a bis-(chlorotriazine) (VII) which finally is reacted with a diamine (VIII) so as ultimately to give a compound of the formula (I), in which $R_1$—X— is different from chlorine.

The three stages of the reaction can be carried out in one and the same reactor, in a single reaction medium, without isolating the intermediates (V) and (VII); however, it is also possible to isolate the intermediates and employ them, after isolation, in the next reaction.

The second alternative of the process provides the following three reaction stages:

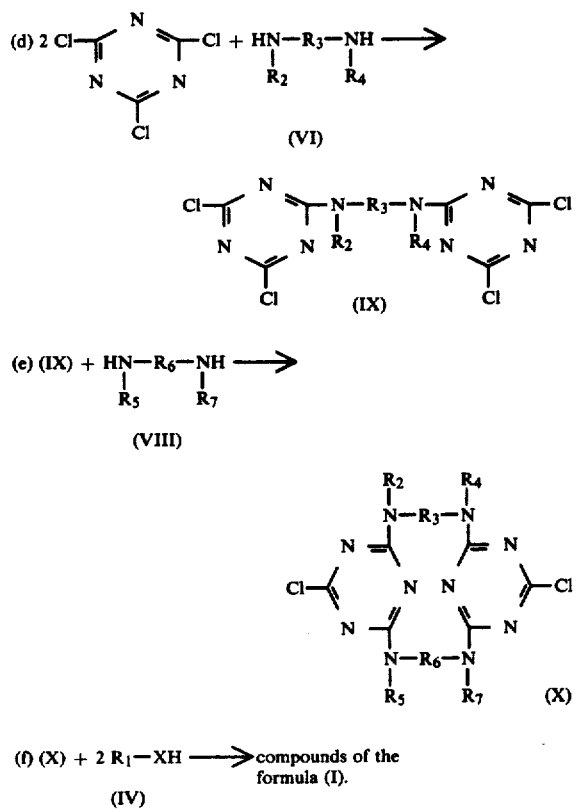

(f) (X) + 2 $R_1$—XH ⟶ compounds of the formula (I).
         (IV)

This thus comprises the preparation, from cyanuric chloride and a diamine (VI), of a bis-(dichlorotriazine) (IX), which is then reacted with a diamine (VIII), to form a macrocyclic dichlorotriazine (X) which, finally, by reaction with (IV) gives a compound of the formula (I), in which $R_1$—X— is different from chlorine.

The three stages of this process can be carried out in one and the same reactor in a single reaction medium, without isolating the intermediates (IX) and (X), but it is also possible, and in some cases preferable, to separate off the said intermediates and employ them, after isolation, in the next reaction.

In the above reaction schemes, $R_1$, $R_2$, $R_3$, $R_4$, $R_5$, $R_6$ and $R_7$ are as defined at the outset.

Both the processes are carried out using inert solvents, for example acetone, methyl ethyl ketone, ether, dioxane, tetrahydrofuran, benzene, toluene, xylene, trimethylbenzene, ethylbenzene, tetralin, decalin, octane or decane.

In ordr to fix the hydrochloric acid liberated in the process, the reaction is carried out, in each case, in the presence of organic or inorganic bases, for example triethylamine, tributylamine, sodium hydroxide, potassium hydroxide, sodium carbonate or potassium carbonate, working at a temperature of between −30° C. and 30° C., preferably between −10° C. and 20° C., for reactions (a) and (d), between 30° C. and 100° C., preferably between 40° C. and 80° C., for reactions (b) and (e), and between 100° C. and 200° C., preferably between 120° C. and 180° C., for reactions (c) and (f).

Reaction (f) if carried out using the isolated intermediate (X) can also be carried out using, as the solvent, an excess of the reagent (IV); when X is >O or >S, it is possible to use, as the reagent, the alkali metal derivative $R_1$—X—M, where M is sodium or potassium, in the absence of an added base, whilst, when X is >N—$R_8$, it is possible to use an excess of the reagent (IV) as the base.

The reagents are preferably employed in the stoichiometric ratio but it is also possible to employ an excess of up to 10% relative to the theoretical amount. In reaction (f) it is possible to employ a large excess, for example up to 30 times the theoretical amount, of the reagent (IV) which, as already mentioned, can also be used as the solvent in the said reaction.

We have also found that a preferred condition for obtaining the compounds of the formula (I) is to use a high solvent/reagent ratio in the cyclisation stages (c) and (e), which ratio should be between 6:1 and 100:1, preferably between 6:1 and 20:1.

In the other stages, (a), (b), (d) and (f), the solvent: reagent ratio is non-critical and can thus vary within wide limits, for example between 1:1 and 20:1.

The compounds of the formula (I) has obtained are isolated from the reaction mixture by using the normal purification processes, for example by crystallisation or by washing with suitable solvents.

As mentioned at the outset, the compounds of the formula (I) are very effective in improving the light stability, heat stability and oxidation stability of synthetic polymers, for example high density and low density polyethylene, polypropylene, ethylene/propylene copolymers, ethylene/vinyl acetate copolymers, polybutadiene, polyisoprene, polystyrene, butadiene/styrene copolymers, acrylonitrile/butadiene/styrene copolymers, vinyl chloride/vinylidene polymers and copolymers, polyoxymethylene, polyurethanes, saturated and unsaturated polyesters, polyamides, polycarbonates, polyacrylates, alkyd resins and epoxide resins.

The compounds of the formula (I) can be mixed with the synthetic polymers in various proportions depending on the nature of the polymer, the end use and the presence of other additives. In general, it is advantageous to employ from 0.01 to 5% by weight of the compounds of the formula (I), based on the weight of the polymers, preferably from 0.05% to 1%.

The compounds of the formula (I) can be incorporated into the polymeric materials by various processes, such as dry blending in the form of powders, or wet mixing in the form of solutions or suspensions, or mixing in the form of a master batch; in these operations, the synthetic polymer can be employed in the form of a powder, granules, a solution, a suspension or an emulsion. The polymers stabilised with the products of the formula (I) can be used for the preparation of moulded articles, films, tapes, fibres, monofilaments, surface coatings and the like. If desired, other additives can be added to the mixtures of the compounds of the formula (I) with the synthetic polymers, such as antioxidants, ultraviolet absorbers, nickel stabilisers, pigments, fillers, plasticisers, antistatic agents, flameproofing agents, lubricants, anti-corrosion agents and metal deactivators.

Examples of the additives which can be mixed with the compounds of the formula (I) are, in particular:

Phenolic antioxidants: for example 2,6-di-t-butyl-p-cresol, 4,4'-thio-bis-(3-methyl-6-t-butyl-phenol), 1,1,3-tris-(2-methyl-4-hydroxy-5-t-butylphenyl)-butane, octadecyl 3-(3,5-di-t-butyl-4-hydroxyphenyl)-propionate, pentaerythritol tetrakis-3-(3,5-di-t-butyl-4-hydroxyphenyl)-propionate, tris-(3,5-di-t-butyl-4-hydroxybenzyl)-isocyanurate and tris-(4-t-butyl-3-hydroxy-2,6-dimethylbenzyl)-isocyanurate;

Secondary antioxidants, such as esters of thiodipropionic acid, for example di-n-dodecyl thiodipropionate and di-n-octadecyl thiodipropionate; aliphatic sulfides and disulfides, for example di-n-dodecyl sulfide, di-n-octadecyl sulfide and di-n-octadecyl disulfide; aliphatic, aromatic or aliphatic-aromatic phosphites and thiophosphites, for example tri-n-dodecyl phosphite, tris-(nonylphenyl)phosphite, tri-n-dodecyl trithiophosphite, phenyl di-n-decyl phosphite, di-n-octadecyl pentaerythritol diphosphite, tris(2,4-di-t-butylphenyl)phosphite and tetrakis-(2,4-di-t-butylphenyl)4,4'-biphenylenediphosphonite;

Ultraviolet absorbers, for example 2-hydroxy-4-n-octyloxybenzophenone, 2-hydroxy-4-n-dodecyloxybenzophenone, 2-(2-hydroxy-3,5-di-t-butylphenyl)-5-chlorobenzotriazole, 2-(2-hydroxy-3,5-di-t-amylphenyl)-benzotriazole, 2,4-di-t-butylphenyl 3,5-di-t-butyl-4-hydroxybenzoate, hexadecyl 3,5-di-t-butyl-4-hydroxybenzoate, phenyl salicylate, p-t-butylphenyl salicylate, 2-ethoxy-2'-ethyl-oxanilide, 2-ethoxy-5-t-butyl-2'-ethyl-oxanilide and 2-ethoxy-2'-ethyl-5,5'-di-t-butyl-oxanilide;

Piperidine-based light stabilisers, for example 2,2,6,6-tetramethyl-piperid-4-yl benzoate, bis-(2,2,6,6-tetramethyl-piperid-4-yl)sebacate, bis-(1,2,2,6,6-pentamethyl-piperid-4-yl)sebacate, bis-(1,2,2,6,6-pentamethylpiperid-4-yl)butyl-3,5-di-t-butyl-4-hydroxybenzyl-malonate, piperidyl derivatives of triazine polymers of the type described in U.S. Pat. No. 4,086,204 and piperidine polyesters of the type described in U.S. Pat. No. 4,233,412;

Light stabilisers based on nickel, for example Ni monoethyl 3,5-di-t-butyl-4-hydroxybenzyl-phosphonate, the butylamine-Ni 2,2'-thio-bis-(4-t-octylphenolate) complex, Ni 2,2'-thio-bis-(4-t-octylphenolphenolate), Ni dibutyl-dithiocarbamate, Ni 3,5-di-t-butyl-4-hydroxybenzoate and the Ni complex of 2-hydroxy-4-n-octyloxybenzophenone;

Organo-tin stabilisers, for example dibutyl-tin maleate, dibutyl-tin laurate and dioctyl-tin maleate;

Acrylic esters, for example ethyl α-cyano-β, β-diphenylacrylate and methyl α-cyano-β-methyl-4-methoxycinnamate;

Metal salts of the higher fatty acids, for example calcium stearate, barium stearate, cadmium stearate, zinc stearate, lead stearate, nickel stearate, calcium laurate, cadmium laurate, zinc laurate and barium laurate;

Organic and inorganic pigments, for example Colour Index Pigment Yellow 37, Colour Index Pigment Yellow 83, Colour Index Pigment Red 144, Colour Index Pigment Red 48:3, Colour Index Pigment Blue 15, Colour Index Pigment Green 7, titanium dioxide, iron oxide and the like.

Because of their low volatility and their low tendency to migrate, the compounds of the present invention are particularly useful as light stabilisers for polyolefine articles of low thickness, such as fibres, tapes and films, which, during processing and use, can suffer a more or less rapid loss of stabiliser due to evaporation, blooming or to extraction by water, particularly in the presence of surfactants.

In order to illustrate the present invention more clearly, there will be described some examples of the preparation of the compounds of the formula (I), which examples are given by way of illustration and do not imply any limitation.

EXAMPLE 1

A solution of 14.6 g (0.2 mol) of diethylamine in 50 ml of water is added slowly, whilst keeping the temperature at between $-10°$ C. and $0°$ C., to a solution of 36.9 g (0.2 mol) of cyanuric chloride in 800 ml of xylene, cooled to $-10°$ C. After 30 minutes, a solution of 8.4 g of sodium hydroxide in 50 ml of water is added, still at between $-10°$ C. and $0°$ C.

The mixture is stirred for 1 hour at about $0°$ C., 35.2 g (0.1 mol) of N,N'-bis-(2,2,6,6-tetramethyl-piperid-4-yl)-trimethylenediamine and 32 g of sodium hydroxide are added, and the whole is heated for 4 hours at $60°$ C. 35.2 g (0.1 mol) of N,N'-bis-(2,2,6,6-tetramethyl-piperid-4-yl)-trimethylenediamine are then added and the mixture is heated under reflux for 16 hours. After cooling, the reaction mixture is filtered to remove the inorganic products, the filtrate is evaporated to dryness and the residue obtained is washed twice with boiling acetone and is finally dried.

On the basis of the analytical data, the product obtained has the following structural formula:

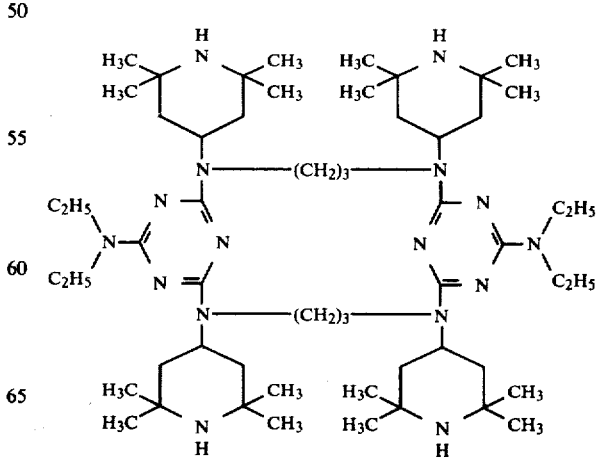

Melting point = 334°-7° C.
Molecular weight (vapour pressure osmometry) = 970 (theory: 1001.5)
Analyses for $C_{56}H_{104}N_{16}$: calculated: C 67.16%, H 10.47%, N 22.37%; found: C 67.10%, H 10.45%, N 22.45%.

EXAMPLES 2–13

Following the procedure described in Example 1, the compounds of Examples 2–13, of the general formula (XI), were prepared:

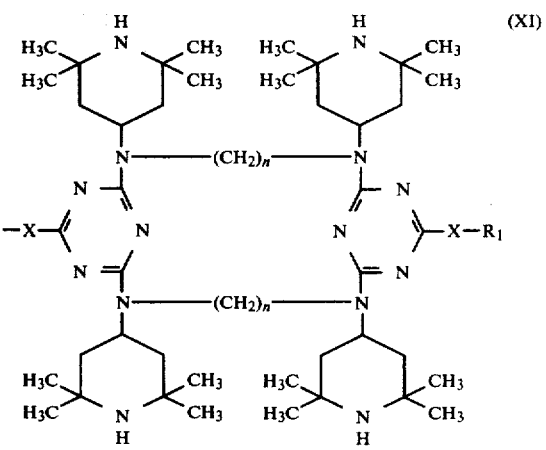

(XI)

| Example No. | $R_1$—X— | n | Melting point | Formula | Analyses calculated | found |
|---|---|---|---|---|---|---|
| 2 | $C_2H_5$<br>$\phantom{C_2H_5}$N—<br>$C_2H_5$ | 6 | >350° C. | $C_{62}H_{116}N_{16}$ | C = 68.59%<br>H = 10.77%<br>N = 20.64% | 68.15%<br>10.72%<br>20.65% |
| 3 | $(CH_3)_2$—CH<br>$\phantom{(CH_3)_2}$N—<br>$(CH_3)_2$—CH | 6 | 320–323° C. | $C_{66}H_{124}N_{16}$ | C = 69.43%<br>H = 10.94%<br>N = 19.63% | 68.86%<br>10.90%<br>19.31% |
| 4 | $\phantom{CH_3—CH_2—}CH_3$<br>$CH_3—CH_2—CH$<br>$\phantom{CH_3—CH_2—CH}$N—<br>$CH_3—CH_2—CH$<br>$\phantom{CH_3—CH_2—}CH_3$ | 6 | 298–301° C. | $C_{70}H_{132}N_{16}$ | C = 70.18%<br>H = 11.11%<br>N = 18.71% | 69.57%<br>11.02%<br>18.55% |
| 5 | $\phantom{CH_3—}CH_3\phantom{—CH_2—}CH_3$<br>$CH_3—C—CH_2—C—NH—$<br>$\phantom{CH_3—}CH_3\phantom{—CH_2—}CH_3$ | 6 | 315–317° C. | $C_{70}H_{132}N_{16}$ | C = 70.18%<br>H = 11.11%<br>N = 18.71% | 70.25%<br>11.15%<br>18.49% |
| 6 | cyclohexyl-NH— | 3 | 218–220° C. | $C_{60}H_{108}N_{16}$ | C = 68.40%<br>H = 10.33%<br>N = 21.27% | 67.95%<br>10.25%<br>20.85% |
| 7 | cyclohexyl-NH— | 6 | >350° C. | $C_{66}H_{120}N_{16}$ | C = 69.67%<br>H = 10.63%<br>N = 19.70% | 69.72%<br>10.60%<br>19.89% |
| 8 | $CH_3—(CH_2)_3—CH—CH_2—NH—$<br>$\phantom{CH_3—(CH_2)_3—}CH_2—CH_3$ | 6 | 303–305° C. | $C_{70}H_{132}N_{16}$ | C = 70.18%<br>H = 11.11%<br>N = 18.71% | 70.31%<br>10.99%<br>18.60% |
| 9 | (cyclohexyl)$_2$N— | 6 | >350° C. | $C_{78}H_{140}N_{16}$ | C = 71.95%<br>H = 10.84%<br>N = 17.21% | 71.02%<br>10.63%<br>17.08% |

-continued

| Example No. | R₁—X— | n | Melting point | Formula | Analyses calculated | found |
|---|---|---|---|---|---|---|
| 10 | cyclohexyl-N(H)-(2,2,6,6-tetramethylpiperid-4-yl)- | 6 | >350° C. | $C_{84}H_{154}N_{18}$ | C = 71.24%<br>H = 10.96%<br>N = 17.80% | 70.93%<br>10.94%<br>17.64% |
| 11 | n-C₄H₉—N(H)-(2,2,6,6-tetramethylpiperid-4-yl)- | 6 | 346–348° C. | $C_{80}H_{150}N_{18}$ | C = 70.44%<br>H = 11.08%<br>N = 18.48% | 70.39%<br>11.07%<br>18.37% |
| 12 | n-C₈H₁₇—N(H)-(2,2,6,6-tetramethylpiperid-4-yl)- | 2 | 345–348° C. | $C_{80}H_{150}N_{18}$ | C = 70.44%<br>H = 11.08%<br>N = 18.48% | 70.07%<br>11.07%<br>18.38% |
| 13 | n-C₄H₉—N(H)-(2,2,6,6-tetramethylpiperid-4-yl)- | 2 | >350° C. | $C_{72}H_{134}N_{18}$ | C = 69.07%<br>H = 10.79%<br>N = 20.14% | 68.18%<br>10.65%<br>20.10% |

EXAMPLE 14

39.4 g (0.1 mol) of N,N'-bis-(2,2,6,6-tetramethylpiperid-4-yl)-hexamethylenediamine is added in the course of about 1 hour, without exceeding 0° C, to a solution of 36.9 g (0.2 mol) of cyanuric chloride in 1,000 ml of acetone, cooled to −10° C. When the addition is complete, the mixture is stirred at about 0° C. for 30 minutes, after which a solution of 8 g of sodium hydroxide dissolved in 30 ml of water is added slowly, whilst keeping the temperature at about 0° C.

After 1 hour at about 0° C., 39.4 g (0.1 mol) of N,N'-bis-(2,2,6,6-tetramethyl-piperid-4-yl)-hexamethylenediamine and 8 g of sodium hydroxide dissolved in 30 ml of water are added and the mixture is heated under reflux for 4 hours. After cooling, the precipitate obtained is filtered off, washed first with acetone and then with water, and finally dried.

On the basis of the analytical data, the product has the following structural formula:

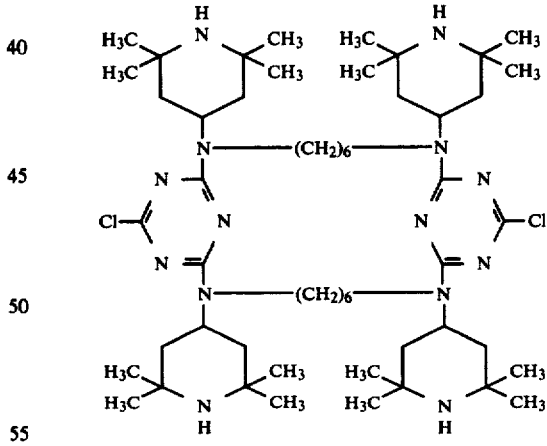

Melting point = >350° C.

Molecular weight (vapour pressure osmometry) = 1,050 (theory: 1,012.3).

Analyses for $C_{54}H_{96}Cl_2N_{14}$: calculated: C 64.07%; H 9.56%; N 19.37%; Cl 7.00%; found: C 63.83%; H 9.48%; N 19.21%; Cl 7.09%.

EXAMPLE 15

The compound of the formula

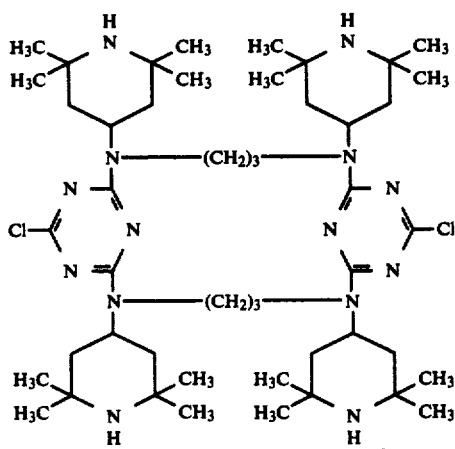

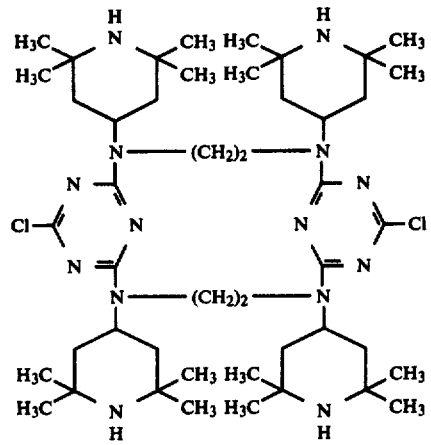

was prepared by working as described in Example 14. Melting point=315°–7° C.

Analyses for $C_{48}H_{84}Cl_2N_{14}$: calculated: C 62.11%; H 9.12%; N 21.13%; Cl 7.64%; found: C 62.06%; H 9.02%; N 21.35%; Cl 7.63%.

EXAMPLE 16

The compound of the formula was prepared by working as described in Example 14. Melting point >350° C.

Analyses for $C_{46}H_{80}Cl_2N_{14}$: calculated: C 61.38%; H 8.96%; N 21.78%; Cl 7.88%; found: C 60.87%; H 8.91%; N 21.57%; Cl 7.89%.

EXAMPLE 17

50.6 g (0.05 mol) of the compound described in Example 14, 22.2 g (0.12 mol) of n-dodecylamine, 8 g of sodium hydroxide and 300 ml of xylene are heated under reflux for 20 hours. The mixture is filtered hot; on cooling, a crystalline product precipitates, which is filtered off, washed with hexane and dried. On the basis of the analytical data, the product has the following structural formula:

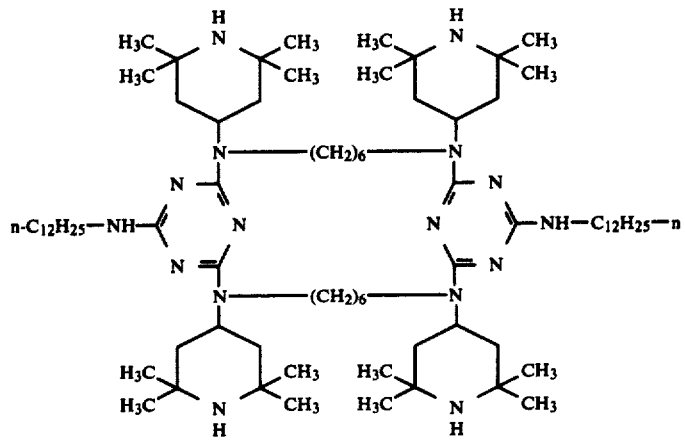

Melting point=252° C.

Analyses for $C_{78}H_{148}N_{16}$: calculated: C 71.51%; H 11.39%; N 17.10%; found: C 71.39%; H 11.29%; N 16.92%.

EXAMPLES 18–24

The following compounds of the formula (XI) are prepared by the procedure described in Example 17:

| Example No. | $R_1$—X— | n | Melting point | Formula | Analyses calculated | found |
|---|---|---|---|---|---|---|
| 18 | n-$C_8H_{17}$—NH— | 6 | 298–301° C. | $C_{70}H_{132}N_{16}$ | C = 70.18% <br> H = 11.11% <br> N = 18.71% | 70.11% <br> 11.06% <br> 18.72% |

-continued

| Example No. | R₁—X— | n | Melting point | Formula | Analyses calculated | found |
|---|---|---|---|---|---|---|
| 19 | n-C₄H₉\N—<br>n-C₄H₉/ | 6 | >350° C. | C₇₀H₁₃₂N₁₆ | C = 70.18%<br>H = 11.11%<br>N = 18.71% | 69.62%<br>11.07%<br>18.68% |
| 20 | (CH₂)₆ N— | 6 | >350° C. | C₆₆H₁₂₀N₁₆ | C = 69.67%<br>H = 10.63%<br>N = 19.70% | 69.46%<br>10.65%<br>19.84% |
| 21 | n-C₈H₁₇—N—<br>(tetramethylpiperidine) | 6 | 274–275° C. | C₈₈H₁₆₆N₁₈ | C = 71.59%<br>H = 11.33%<br>N = 17.08% | 71.40%<br>11.23%<br>16.98% |
| 22 | CH₃—(CH₂)₃—O—(CH₂)₂—O— | 2 | 232–233° C. | C₅₈H₁₀₆N₁₄O₄ | C = 65.50%<br>H = 10.04%<br>N = 18.44% | 64.43%<br>9.87%<br>18.37% |
| 23 | (2,2,6,6-tetramethylpiperidin-4-yl)oxy— | 3 | 179–181° C. | C₆₆H₁₂₀N₁₆O₂ | C = 67.77%<br>H = 10.34%<br>N = 19.16% | 66.70%<br>10.16%<br>18.87% |
| 24 | (1,2,2,6,6-pentamethylpiperidin-4-yl)O—(CH₂)₃—NH— | 3 | 141–142° C. | C₇₄H₁₃₈N₁₈O₂ | C = 67.74%<br>H = 10.60%<br>N = 19.22% | 67.66%<br>10.54%<br>19.19% |

EXAMPLE 25

50.6 g (0.05 mol) of the compound described in Example 14 and a solution of 3.5 g of sodium in 200 ml of n-butyl alcohol are heated under reflux for 30 hours. The reaction mixture is evaporated to dryness and the residue is washed with water and dried. On the basis of the analytical data, the product obtained has the following structural formula:

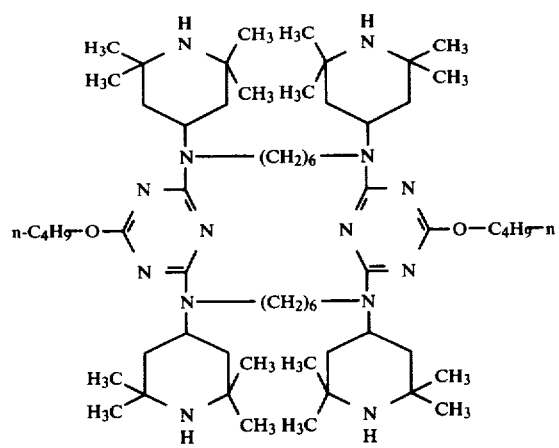

Melting point = 336°–9° C.

Analyses for C₆₂H₁₁₄N₁₄O₂: calculated: C 68.47%; H 10.56%; N 18.03%; found: C 67.79%; H 10.66%; N 18.02%.

EXAMPLE 26

A solution of 36.8 g (0.2 mol) of 2,2,6,6-tetramethyl-4-ethylaminopiperidine is added slowly, whilst keeping the temperature below 10° C., to a solution of 36.9 g (0.2 mol) of cyanuric chloride in 1,000 ml of xylene cooled to 0° C. After 30 minutes at 5°–10° C., a solution of 8.4 g of sodium hydroxide in 30 ml of water is added. The mixture is stirred for 1 hour at 5°–10° C., 7.4 g (0.1 mol) of trimethylenediamine and 8.4 g of sodium hydroxide dissolved in 30 ml of water are added and the whole is heated at 60° for 4 hours. A further 7.4 g (0.1 mol) of trimethylenediamine and 24 g of sodium hydroxide are then added and the mixture is heated under reflux for 16 hours. After cooling, the mixture is filtered to remove the inorganic products, the filtrate is evaporated to dryness and the residue obtained is washed twice with boiling acetone and is dried.

On the basis of the analytical data, the product obtained has the following structural formula:

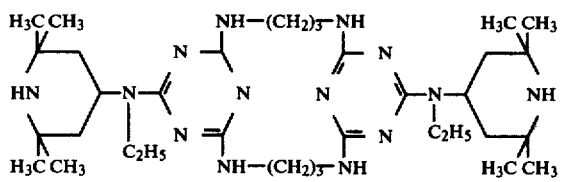

Melting point = 281°-3° C.

Analyses for C₃₄H₆₂N₁₄: calculated: C 61.23%; H 9.37%; N 29.40%; found: C 60.87;1 %; H 9.25%; N 29.12%.

EXAMPLE 27

26.1 g (0.02 mol) of the compound prepared according to Example 17, 15.7 g (0.3 mol) of 88% formic acid, 24.3 g (0.3 mol) of 37% aqueous formaldehyde and 50 ml of water are heated under reflux for 10 hours. After cooling, the mixture is diluted with 100 ml of water and 20 g of sodium hydroxide dissolved in 50 ml of water are added. The precipitate obtained is filtered off, washed with water until the pH is neutral, dried and crystallised from octane.

On the basis of the analytical data, the product obtained has the following structural formula:

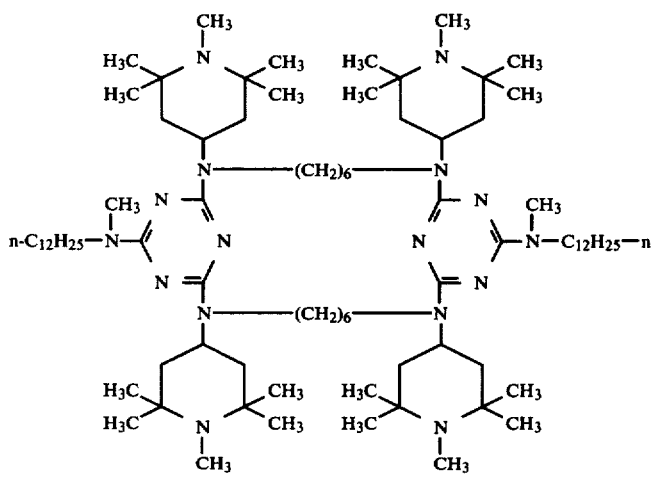

Melting point = 238°-9° C.

Analyses for C₈₄H₁₆₀N₁₆: calculated: C 72.36%; H 11.56%; N 16.07%; found: C 71.54%; H 11.50%; N 16.02%.

EXAMPLE 28

42.4 g (0.2 mol) of 2,2,6,6-tetramethyl-4-n-butylaminopiperidine is added slowly, whilst keeping the temperature at between 10° C. and 20° C., to a solution of 36.9 g (0.2 mol) of cyanuric chloride in 1200 ml of xylene, cooled to 10° C. After 30 minutes, a solution of 8.4 g of sodium hydroxide in 30 ml of water is added, still at between 10° C. and 20° C. The mixture is stirred for 1 hour at about 20° C., 39.4 g (0.1 mol) of N,N'-bis-(2,2,6,6-tetramethyl-piperid-4-yl)-hexamethylenediamine and a solution of 8.4 g of sodium hydroxide in 30 ml of water is added and the whole is heated for 4 hour at 60° C. 11.6 g (0.1 mol) of hexamethylenediamine and 12 g of sodium hydroxide are then added and the mixture is heated under reflux for 16 hours. After cooling, the reaction mixture is filtered to remove the inorganic products, the filtrate is evaporated to dryness and the residue obtained as washed first with acetone and then with boiling acetone, and finally dried.

On the basis of the analytical data, the product has the following structural formula:

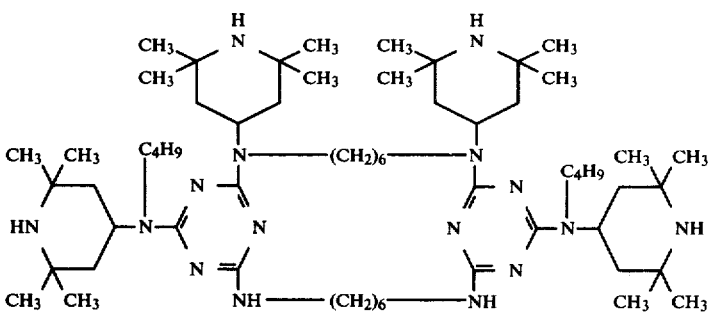

Melting point = 276°-8° C.

Analyses for C₆₂H₁₁₆N₁₆: calculated: C 68.59%, H 10.77%, N 20.64%; found: C 67.22%, H 10.56%, N 20.34%.

EXAMPLE 29

45 g (0.005 mol) of the compound described in Example 16, 65 g (0.5 mol) of 3-diethylaminopropylamine, 300 ml of xylene and 16 g of sodium hydroxide are heated under reflux for 16 hours. The reaction mixture is filtered hot; on cooling a crystalline product precipitates, which is filtered off and dried.

On the basis of the analytical data, the product has the following structural formula:

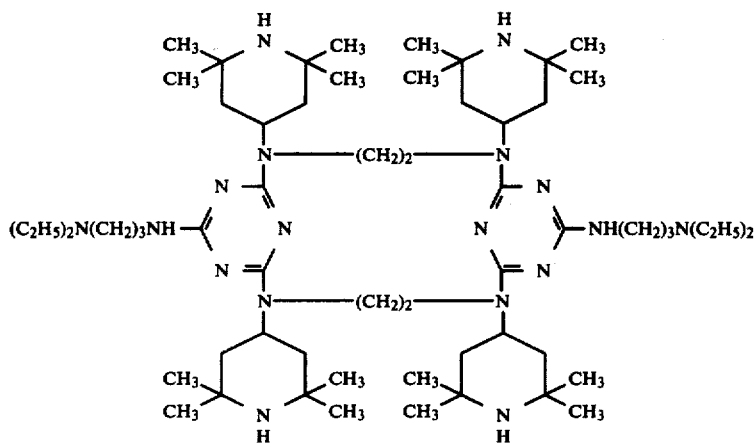

Melting point: 275°–280° C.

Analyses for $C_{60}H_{114}N_{18}$: calculated: C 66.26%, H 10.56%, N 23.18%; found: C 65.72%, H 10.29%, N 22.82%.

The efficiency, as stabilisers, of the products prepared according to the present invention is illustrated in the examples which follow, in which some of the products obtained in the preparation examples are employed for stabilising polypropylene fibres and tapes and low density and high density polyethylene films.

EXAMPLE 30

2.5 g of the compounds indicated in Table 1, 0.5 g of n-octadecyl 3-(3,5-di-t-butyl-4-hydroxyphenyl)-propionate (antioxidant) and 1 g of calcium stearate are intimately mixed with 1,000 g of polypropylene of melt index 13 (®Propathene HF 100, a product of Imperial Chemical Industries).

The mixture is then extruded at a temperature of 200°–230° C. and converted to granules, from which fibres are obtained by melt spinning under the following working conditions:

extruder temperature: 230°–250° C.
spinneret temperature: 240° C.
stretch ratio: 1:3
count: 20 deniers per fibre The fibres obtained are exposed, on a white card, in a Weather-Ometer 65 WR (ASTM G 27-70), with a black panel temperature of 63° C. Samples are taken periodically, and the residual tenacity is measured on these by means of a constant-speed tensometer; the exposure time ($T_{50}$) needed to halve the initial tenacity is then evaluated.

Table 1 shows the results obtained.

TABLE 1

| Stabiliser | $T_{50}$ (hours) |
| --- | --- |
| Without light stabiliser | 130 |
| Compound of Example 1 | 1,400 |
| Compound of Example 2 | 1,070 |
| Compound of Example 3 | 980 |
| Compound of Example 5 | 950 |
| Compound of Example 6 | 1,280 |
| Compound of Example 7 | 1,500 |
| Compound of Example 11 | 1,600 |
| Compound of Example 12 | 1,290 |
| Compound of Example 17 | 1,030 |
| Compound of Example 18 | 1,050 |
| Compound of Example 25 | 1,120 |

TABLE 1-continued

| Stabiliser | $T_{50}$ (hours) |
| --- | --- |
| Compound of Example 27 | 1,200 |

EXAMPLE 31

2 g of the compounds indicated in Table 2, 1 g of pentaerythritol tetrakis-3-(3,5-di-t-butyl-4-hydroxyphenyl)-propionate (antioxidant) and 1 g of calcium stearate are intimately mixed with 1,000 g of polypropylene of melt index 3 (®Propathene HF 22, a product of Imperial Chemical Industries).

The mixture obtained is then extruded at a temperature of 200°–230° C. and converted to granules, from which tapes of thickness 40 μm and width 3 mm are obtained under the following working conditions:

extruder temperature: 230°–240° C.
head temperature: 240° C.
stretch ratio: 1:6

The tapes obtained are exposed, on a white card, in a Weather-Ometer 65 WR (ASTM G 27-70), with a black panel temperature of 63° C.

Samples are taken periodically, and the residual tenacity is measured on these by means of a constant-speed tensometer; the exposure time ($T_{50}$) needed to halve the initial tenacity is then evaluated.

Table 2 shows the results obtained.

TABLE 2

| Stabiliser | $T_{50}$ (hours) |
| --- | --- |
| Without light stabiliser | 230 |
| Compound of Example 1 | 1,410 |
| Compound of Example 2 | 1,180 |
| Compound of Example 3 | 1,020 |
| Compound of Example 5 | 960 |
| Compound of Example 6 | 1,520 |
| Compound of Example 7 | 1,470 |
| Compound of Example 11 | 1,620 |
| Compound of Example 12 | 1,490 |
| Compound of Example 17 | 1,200 |
| Compound of Example 18 | 1,460 |
| Compound of Example 25 | 1,260 |
| Compound of Example 27 | 1,520 |

EXAMPLE 32

2 g of each of the compounds indicated in Table 3 are thoroughly mixed with 1000 g of high density polyethylene of melt index 0.4 (®Hostalen GF 7660, a product of Hoechst AG), 0.3 g of n-octadecyl 3-(3,5-di-t-butyl-4-hydroxyphenyl)propionate (antioxidant) and 1 g of calcium stearate.

The mixture obtained is then extruded at a temperature of 190° C. and converted to granules from which sheets of 0.2 mm thickness are produced by compression moulding at 200° C. The sheets are exposed in a Weather-Ometer 65 WR with a black panel temperature of 63° C.

The time (T 0.1) required to have an increase in the content of carbonyl groups of 0.1% at 5.85 micrometers is determined.

For comparison sheets are prepared under the same conditions, but without addition of a light stabilizer.

The results obtained are recorded in Table 3.

TABLE 3

| Stabiliser | T 0.1 (hours) |
|---|---|
| Without light stabiliser | 350 |
| Compound of example 5 | 3150 |
| Compound of example 6 | 3920 |
| Compound of example 8 | 2940 |
| Compound of example 17 | 3630 |
| Compound of example 21 | 4060 |
| Compound of example 22 | 3800 |

EXAMPLE 33

In each case, 2 g of one of the compounds indicated in Table 4 and 0.3 g of octadecyl 3-(3,5-di-t-butyl-4-hydroxyphenyl)-propionate (antioxidant) are intimately mixed with 1000 g of low-density polyethylene of melt index 0.6 (®Fertene EF 3-2000, a product of Societa Montedison).

The mixture is then extruded at 190° C. and converted to granules from which sheets of 0.2 mm thickness are obtained by compression-moulding at 200° C. and are exposed on white cardboard in a Weather-Ometer 65 WR (ASTM G 27-70) with a black panel temperature of 63° C.

The time (T 0.2) required to have an increase in the content of carbonyl groups of 0.2% at 5.85 micrometers is determinated.

By way of comparison sheets of polymers are prepared, under the same conditions, but without the addition of light stabiliser.

The results obtained are recorded in table 4.

TABLE 4

| Stabiliser | T 0.2 (hours) |
|---|---|
| Without light stabiliser | 750 |
| Compound of example 1 | 6760 |
| Compound of example 5 | 6310 |
| Compound of example 6 | 5620 |
| Compound of example 17 | 5870 |
| Compound of example 18 | 5660 |
| Compound of example 21 | 6700 |
| Compound of example 25 | 6520 |
| Compound of example 27 | 4860 |

What is claimed is:
1. A compound of the formula (I)

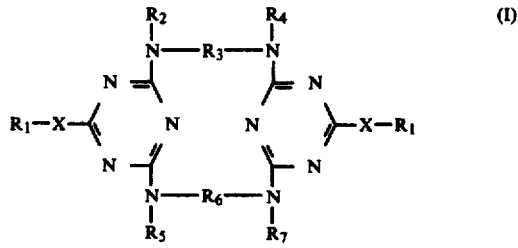

in which $R_1$ is hydrogen, $C_1-C_{18}$-alkyl, $C_3-C_{18}$-alkenyl, $C_5-C_{18}$-cycloalkyl, substituted or unsubstituted $C_6-C_{18}$-aryl, substituted or unsubstituted $C_7-C_{18}$-aralkyl, an $-R_8-Y$ radical, in which $R_8$ is $C_2-C_6$-alkylene and $Y$ is $-O-R_9$ or

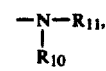

$R_9$ being hydrogen or $C_1-C_{18}$-alkyl and $R_{10}$ and $R_{11}$, which may be identical or different, being $C_1-C_6$-alkyl, 2,2,6,6-tetramethyl-piperid-4-yl or 1,2,2,6,6-pentamethyl-piperid-4-yl, or $R_1$ is a radical of the formula (II)

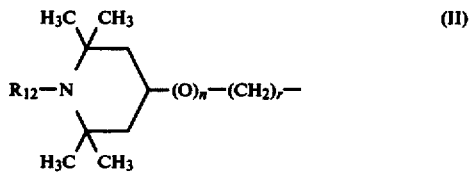

in which n is zero or 1, r is zero, 1, 2 or 3, $R_{12}$ is hydrogen, $C_1-C_{12}$-alkyl, $C_3-C_{12}$-alkenyl or -alkynyl, substituted or unsubstituted $C_7-C_{12}$-aralkyl, $C_1-C_{12}$-acyl, 2,3-epoxypropyl or

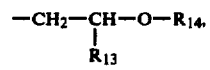

in which $R_{13}$ is hydrogen, methyl, ethyl or phenyl and $R_{14}$ is hydrogen, $C_1-C_{12}$-alkyl, $C_3-C_{12}$-alkenyl, $C_7-C_{12}$-aralkyl or $C_1-C_{12}$-acyl, or $R_1$ is a radical of the formula (III)

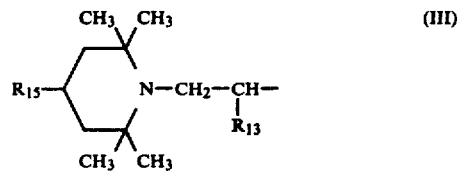

in which $R_{15}$ is hydrogen, $C_1-C_8$-alkoxy, $C_3-C_8$-alkenyloxy or benzyloxy and $R_{13}$ is as defined above, and X is $>O$, $>S$ or $>N-R_{16}$, in which $R_{16}$ has the same meaning as $R_1$, and the radical $R_1-X-$, considered as a whole, can also be chlorine or pyrrolidin-1-yl, piperid-1-yl or hexahydroazepin-1-yl, $R_2$, $R_4$, $R_5$ and $R_7$, which may be identical or different, are hydrogen, $C_1-C_{12}$-alkyl, $C_2-C_6$-hydroxyalkyl, $C_3-C_{12}$-alkenyl, $C_5-C_{12}$-cycloalkyl, substituted or unsubstituted $C_6-C_{12}$-aryl, substituted or unsubstituted $C_7-C_{12}$-aralkyl or a radical of the formula (II), and $R_3$ and $R_6$, which may be identical or different, are $C_2$–$C_{12}$-alkylene, $C_4$–$C_{12}$-iminodialkylene or -oxadialkylene, $C_5$–$C_{12}$-cycloalkylene, $C_6$–$C_{12}$-arylene or $C_7$–$C_{12}$-aralkylene, and at least one of the radicals $R_1$, $R_2$, $R_4$, $R_5$ and $R_7$ in formula (I) is a radical of the formula (II).

2. A compound of the formula (I) according to claim 1, in which $R_1$ and $R_{16}$, which may be identical or different, are $C_1$–$C_{12}$-alkyl, $C_3$–$C_{12}$-alkenyl, $C_5$–$C_{12}$-cycloalkyl, $C_6$–$C_{12}$-aryl, $C_7$–$C_{12}$-aralkyl, 2,2,6,6-tetramethyl-piperid-4-yl or 1,2,2,6,6-pentamethyl-piperid-4-yl, $R_2$, $R_4$, $R_5$ and $R_7$, which may be identical or different, are $C_1$–$C_{14}$-alkyl, $C_2$–$C_3$-hydroxyalkyl, $C_3$–$C_6$-alkenyl, $C_5$–$C_8$-cycloalkyl, $C_6$–$C_8$-aryl, $C_7$–$C_{12}$-aralkyl, 2,2,6,6-tetramethyl-piperid-4-yl or 1,2,2,6,6-pentamethyl-piperid-4-yl, $R_3$ and $R_6$, which may be identical or different, are $C_2$–$C_6$-alkylene, $C_4$–$C_6$-iminodialkylene or $C_4$–$C_6$-oxadialkylene, $R_8$ is $C_2$–$C_4$-alkylene, $R_9$ is hydrogen or $C_1$–$C_{12}$-alkyl, $R_{10}$ and $R_{11}$, which may be identical or different, are $C_1$–$C_4$-alkyl, 2,2,6,6-tetramethyl-piperid-4-yl or 1,2,2,6,6-pentamethyl-piperid-4-yl, $R_{12}$ is hydrogen, $C_1$–$C_6$-alkyl, $C_3$–$C_6$-alkenyl or -alkynyl, benzyl, $C_1$–$C_6$-acyl, 2,3-epoxypropyl or 2-hydroxyethyl, $R_{13}$ is hydrogen or methyl, $R_{14}$ is hydrogen, $C_1$–$C_6$-alkyl, $C_3$–$C_6$-alkenyl, benzyl or $C_1$–$C_6$-acyl, and $R_{15}$ is hydrogen, $C_1$–$C_6$-alkoxy, allyloxy or benzyloxy, and $R_1$—X—, considered as a whole is chlorine, piperid-1-yl or hexahydroazepin-1-yl.

3. A compound of the formula (I) according to claim 1, in which X is >O or >N-$R_{16}$, $R_1$ and $R_{16}$, which may be identical or different, are hydrogen, $C_2$–$C_{12}$-alkyl, cyclohexyl, 2,2,6,6-tetramethyl-piperid-4-yl or 1,2,2,6,6-pentamethyl-piperid-4-yl, $R_2$, $R_4$, $R_5$ and $R_7$, which may be identical or different, are hydrogen, 2,2,6,6-tetramethyl-piperid-4-yl or 1,2,2,6,6-pentamethyl-piperid-4-yl, $R_3$ and $R_6$ are $C_2$–$C_6$-alkylene, $R_8$ is $C_2$–$C_3$-alkylene, $R_{10}$ and $R_{11}$, which may be identical or different, are $C_1$–$C_4$-alkyl, 2,2,6,6-tetramethyl-piperid-4-yl or 1,2,2,6,6-pentamethyl-piperid-4-yl, $R_{12}$ is hydrogen or methyl and $R_1$—X—, considered as a whole, is chlorine, piperid-1-yl or hexahydroazepin-1-yl.

4. A process for the preparation of a compound of the formula (I)

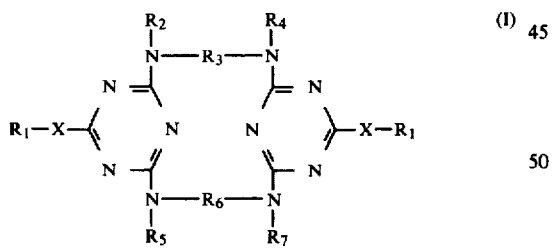
(I)

in which $R_1$ is hydrogen, $C_1$–$C_{18}$-alkyl, $C_3$–$C_{18}$-alkenyl, $C_5$–$C_{18}$-cycloalkyl, substituted or unsubstituted $C_6$–$C_{18}$-aryl, substituted or unsubstituted $C_7$–$C_{18}$-aralkyl, an —$R_8$—Y radical, in which $R_8$ is $C_2$–$C_6$-alkylene and Y is —O—$R_9$ or

$R_9$ being hydrogen or $C_1$–$C_{18}$-alkyl and $R_{10}$ and $R_{11}$, which may be identical or different, being $C_1$–$C_6$-alkyl, 2,2,6,6-tetramethyl-piperid-4-yl or 1,2,2,6,6-pentamethyl-piperid-4-yl, or $R_1$ is a radical of the formula (II)

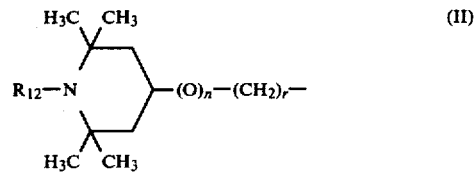
(II)

in which n is zero or 1, r is zero, 1, 2 or 3, $R_{12}$ is hydrogen, $C_1$–$C_{12}$-alkyl, $C_3$–$C_{12}$-alkenyl or -alkynyl, substituted or unsubstituted $C_7$–$C_{12}$-aralkyl, $C_1$–$C_{12}$-acyl, 2,3-epoxypropyl or

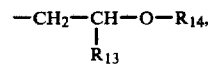

in which $R_{13}$ is hydrogen, methyl, ethyl or phenyl and $R_{14}$ is hydrogen, $C_1$–$C_{12}$-alkyl, $C_3$–$C_{12}$-alkenyl, $C_7$–$C_{12}$-aralkyl or $C_1$–$C_{12}$-acyl, or $R_1$ is a radical of the formula (III)

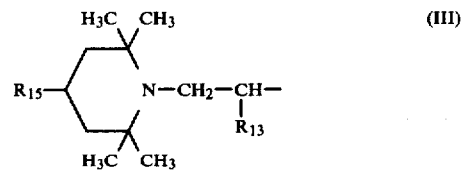
(III)

in which $R_{15}$ is hydrogen, $C_1$–$C_8$-alkoxy, $C_3$–$C_8$-alkenyloxy or benzyloxy and $R_{13}$ is as defined above, and X is >O, >S or >N-$R_{16}$, in which $R_{16}$ has the same meaning as $R_1$, and the radical $R_1$—X—, considered as a whole, can also be chlorine or pyrrolidin-1-yl, piperid-1-yl or hexahydroazepin-1-yl, $R_2$, $R_4$, $R_5$ and $R_7$, which may be identical or different, are hydrogen, $C_1$–$C_{12}$-alkyl, $C_2$–$C_6$-hydroxyalkyl, $C_3$–$C_{12}$-alkenyl, $C_5$–$C_{12}$-cycloalkyl, substituted or unsubstituted $C_6$–$C_{12}$-aryl, substituted or unsubstituted $C_7$–$C_{12}$-aralkyl or a radical of the formula (II), and $R_3$ and $R_6$, which may be identical or different, are $C_2$–$C_{12}$-alkylene, $C_4$–$C_{12}$-iminodialkylene or -oxadialkylene, $C_5$–$C_{12}$-cycloalkylene, $C_6$–$C_{12}$-arylene or $C_7$–$C_{12}$-aralkylene, and at least one of the radicals $R_1$, $R_2$, $R_4$, $R_5$ and $R_7$ in formula (I) is a radical of the formula (II), which comprises reacting cyanuric chloride with a diamine of the formula

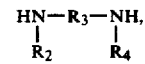

with a diamine of the formula

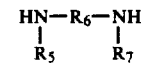

and with a compound of the formula $R_1$-XH, in which $R_1$, $R_2$, $R_3$, $R_4$, $R_5$, $R_6$, $R_7$ and X are as defined above, in three successive stages, in the presence of an inert organic solvent and of an organic or inorganic base present in at least the stoichiometric ratio with respect to the HCl formed in the reaction.

5. A process according to claim 4, wherein the reagents are reacted in accordance with the following succession of stages:

(a) 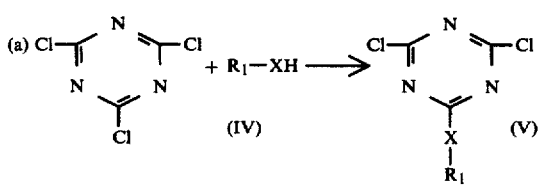

(b) 2 (V) + 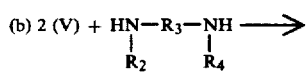

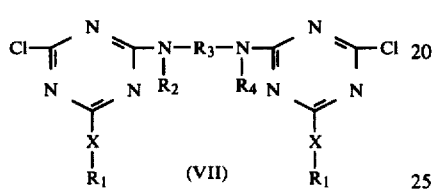

(c) (VII) + 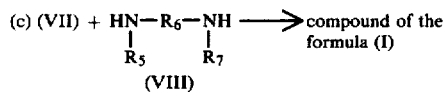 ⟶ compound of the formula (I)

in which $R_1$, $R_2$, $R_3$, $R_4$, $R_5$, $R_6$, $R_7$ and X are as defined above.

6. A process according to claim 4, wherein the reagents are reacted in accordance with the following succession of stages:

(d) 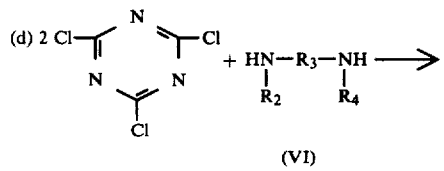

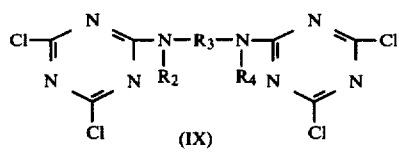

(e) (IX) + 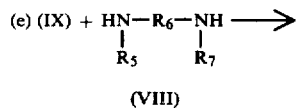

-continued

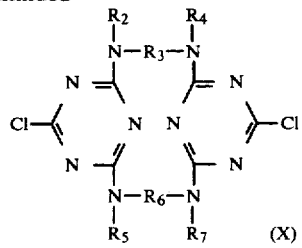

(f) (X) + 2 $R_1$—XH ⟶ compound of the formula (I)
    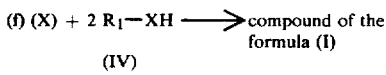

in which $R_1$, $R_2$, $R_3$, $R_4$, $R_5$, $R_6$, $R_7$ and X are as defined above.

7. A process according to any one of claims 4 to 6, wherein the three stages are carried out in one and the same reactor, in a single reaction medium, without isolating the intermediates.

8. A process according to any one of claims 4 to 6, wherein the individual intermediates of the reaction are isolated and employed in the next stage.

9. A process according to claim 4, in which the inert organic solvents are chosen from the group comprising acetone, methyl ethyl ketone, ether, dioxane, tetrahydrofuran, benzene, toluene, xylene, trimethylbenzene, ethylbenzene, tetralin, decalin, octane and decane.

10. A process according to any one of claims 4 to 6, wherein the solvent/reagent ratio in the cyclisation stages (c) and (e) is from 6:1 to 100:1, preferably from 6:1 to 20:1.

11. A process according to claim 4, wherein the reagents are employed in the stoichiometric ratio.

12. A process according to either of claims 5 and 6, wherein the stages (a) and (d) are carried out at a temperature of between −30° C. and 30° C., preferably between −10° C. and 20° C.

13. A process according to either of claims 5 and 6, wherein the stages (b) and (e) are carried out at a temperature of between 30° and 100° C., preferably between 40° and 80° C.

14. A process according to either of claims 5 and 6, wherein the stages (c) and (f) are carried out at a temperature of between 100° and 200° C., preferably between 120° and 180° C.

15. A light-stabilised, heat-stabilised and oxidation-stabilised polymer composition comprising a synthetic polymer and one or more stabilisers of the formula (I) in an amount of between 0.01 and 5%, preferably between 0.05 and 1%, by weight relative to the weight of the synthetic polymer.

16. A composition according to claim 15, which in addition to the novel stabiliser of the formula (I) comprises other conventional additives for synthetic polymers.

17. A composition according to claim 15, wherein the synthetic polymer is polyethylene or polypropylene.

18. A composition according to claim 15, wherein the synthetic polymer is in the form of a fibre, tape or film.

* * * * *